US007357938B2

(12) United States Patent
Stiefel

(10) Patent No.: US 7,357,938 B2
(45) Date of Patent: *Apr. 15, 2008

(54) SULFACETAMIDE FORMULATIONS FOR TREATMENT OF ROSACEA

(75) Inventor: Charles W. Stiefel, Coral Gables, FL (US)

(73) Assignee: Stiefel Laboratories, Inc., Coral Gables, FL (US)

( * ) Notice: Subject to any disclaimer, the term of this patent is extended or adjusted under 35 U.S.C. 154(b) by 637 days.

This patent is subject to a terminal disclaimer.

(21) Appl. No.: 10/937,741

(22) Filed: Sep. 10, 2004

(65) Prior Publication Data

US 2005/0089485 A1    Apr. 28, 2005

Related U.S. Application Data

(63) Continuation-in-part of application No. 10/191,880, filed on Jul. 9, 2002, now Pat. No. 7,022,332.

(60) Provisional application No. 60/304,019, filed on Jul. 9, 2001.

(51) Int. Cl.
*A61K 8/02* (2006.01)
*A61K 8/04* (2006.01)
*A61K 8/06* (2006.01)
*A61K 33/04* (2006.01)

(52) U.S. Cl. ........................ 424/401; 424/59; 424/60; 424/400; 424/703; 514/859; 514/861; 514/863; 514/864

(58) Field of Classification Search .................. 424/59, 424/60, 400, 401, 703; 514/859, 861, 863, 514/864
See application file for complete search history.

(56) References Cited

U.S. PATENT DOCUMENTS

| 4,847,071 | A | 7/1989 | Bissett et al. |
| 4,895,727 | A | 1/1990 | Allen |
| 5,017,366 | A | 5/1991 | Stiefel et al. |
| 5,567,420 | A | 10/1996 | McEleney et al. |
| 6,482,839 | B1 | 11/2002 | Thornfeldt |
| 6,514,489 | B1 | 2/2003 | Shacknai et al. |
| 7,022,332 | B2 * | 4/2006 | Stiefel ........................ 424/401 |
| 2003/0118526 | A1 | 6/2003 | Stiefel |

FOREIGN PATENT DOCUMENTS

| CA | 2161737 A1 | 5/1997 |
| EP | 0692254 | 1/1996 |
| WO | 03/006005 A1 | 1/2003 |

OTHER PUBLICATIONS

Bonnar, E. et al. The Demodex mite population in rosacea, *Journal of the American Academy of Dermatology*, Mar. 1993, pp. 443-448.
Wilkin, J. K. "Flushing Disorders", *Principles and Practice of Dermatology*, Sams and Lynch Editors, 1990, pp. 495-500.
Kelly, A. P. "Rosacea", *Principles and Practice of Dermatology*, Sams and Lynch Editors, 1990, pp. 789-791.
Food and Drug Administration, "Sunscreen Drug Products for Over-The-Counter Human Use", Final Monograph, Federal Register, May 21, 1999, vol. 64, No. 98, pp. 1-54.
Draelos, Z. K., "Sunscreens", *Cosmetics In Dermatology*, Churchill Livingston Inc. (1990), pp. 164-166.
Nichols, K. et al., "Effective Sunscreen Ingredients and Cutaneous Irritation in Patients with Rosacea", *Cutis*, vol. 61, Jun. 1998, pp. 344-346.
"Sunscreen Drug Products for Over-the Counter Human Use; Amendment to the Tentative Final Monograph, Enforcement Policy", 63 Fed. Reg. 56584 (Oct. 22, 1998).
*The United States Pharmacopeia, Twentieth Revision*, Official from Jul. 1, 1980, United States Pharmacopeial Convention, Inc., p. 744.
*Physicians' Desk Reference Sulfacet R® lotion Edition 31*, (1977), pp. 755-756.
"The treatment of rosacea: the safety and efficacy of sodium sulfacetamide 10% and sulfur 5% lotion (Novacet) is demonstrated in a double-blind study", Sauder et al., *J. Derm. Treat.*, (1997) 8, pp. 79-85.
Lebwohl, et al., "The Comparative Efficacy of Sodium Sulfacetamide 10%/Sulfur 5% (Sulfacet-R®) Lotion and Metronidazole 0.75% (MetroGel®) in the Treatment of Rosacea", *J. of Geriatric Dermatology*, 3(5): pp. 183-185 (1995).
Zoe Diana Draelos, MD, PA; "Cosmetics," http://www.emedicine.com/derm/topic502.htm, printed Aug. 8, 2006.
Cosmetic Ingredient Dictionary, "Search Results For: Silica," http://www.cosmeticcop.com/learn/disctionary.asp?keys=silica&pos=1 &type=FIND, printed Aug. 8, 2006.
21 C.F.R. § 352.10 (Apr. 1, 2006 edition), "Subpart B-Active Ingredients,"http://www.access.gpo.gov/nara/cfr/waisidx_06/21cfr352_06.html, printed Aug. 8, 2006.
21 C.F.R. § 352.76 (Apr. 1, 2006), "Determination if a product is water resistant or etc.," http://www.access.gpo.gov/nara/cfr/waisidx_06/21cfr352_06.html, printed Aug. 8, 2006.
Bradley Pharmaceuticals, Inc., "Sulfacet R labeling," http://www.bradpharm.com/intl/dermik.html, printed Aug. 10, 2006.
Bradley Pharmaceuticals, Inc., "Sulfacet R labeling," http://www.bradpharm.com/intl/pdf/SULF2_Ins.pdfhtml, printed Aug. 10, 2006.

(Continued)

*Primary Examiner*—Shelley A. Dodson
(74) *Attorney, Agent, or Firm*—The Nath Law Group; Gary M. Nath; Joshua B. Goldberg

(57) ABSTRACT

A method for treating rosacea in a patient comprising administering to a patient suffering from rosacea a first topical composition comprising at least one sulfacetamide or a derivative thereof and at least one sunscreen, wherein the administration of said first composition provides a more effective treatment of said rosacea in comparison to treatment of rosacea achieved by administration of a second topical composition comprising metronidazole.

43 Claims, No Drawings

OTHER PUBLICATIONS

Lebwohl, et al., "The Comparative Efficacy of Sodium Sulfacetamide 10%/Sulfur 5% (Sulfacet-R®) Lotion and Metronidazole 0.75% (MetroGel®) in the Treatment of Rosacea", *J. of Geriatric Dermatology*, 3:191-195 (1995).

Stanislaw Bucchner, MD., "Rosacea: An Update," Dermatology, 210, pp. 100-108 (2005).

Michelle T. Pelle et al., "Continuing Medical Education: Rosacea: II. Therapy," J. Am. Acad. Dermatol., vol. 51, No. 4, pp. 500-512 (2004).

Wells, F.V. et al., Cosmetics and the Skin. New York: Reinhold Publishing Corp., 1964.

Rieger, Martin M., Ph.D. (Ed.). Harry's Cosmeticology (8th Ed.), New York, NY, Chemical Publishing Co., 2000.

Phenonip(R), product brochure; Clariant UK Ltd.

Rosac(R) Cream With Sunscreen (sodium sulfacetamide 10% and sulfur 5%), product insert, Stiefel Laboratories, Inc.

* cited by examiner

SULFACETAMIDE FORMULATIONS FOR TREATMENT OF ROSACEA

CROSS-REFERENCE TO RELATED APPLICATIONS

This application is a continuation-in-part of U.S. patent application Ser. No. 10/191,880, filed Jul. 9, 2002 now U.S. Pat. 7,022,332, which claims priority to U.S. Provisional Patent Application Ser. No. 60/304,019, filed Jul. 9, 2001, the contents of which are both hereby expressly incorporated by reference in their entirety.

FIELD OF THE INVENTION

The present subject matter relates to sulfactemide formulations for the treatment of rosacea.

BACKGROUND OF THE INVENTION

Rosacea, originally termed acne rosacea, is a chronic inflammatory skin condition primarily affecting the areas of the eyelids, chin, nose, cheeks, and forehead of adults. The condition is characterized by erythema (redness), papules, rhinophyma, telagiectasia, prominent vascularization, dryness, pustules, swelling, lesions, inflammation, infection, enlarged nasal area, hypertrophy of the sebaceous glands, and nodules either singly or in combination in the involved skin areas, primarily in the central areas of the face. Some of these clinical signs, in particular the erythema, are thought to be caused by the dilation of blood vessels. Rosacea may further be characterized by flushing and blushing. In rare instances, rosacea may also occur on the trunk and extremities, such as the chest, neck, back, or scalp.

Eyelids affected by rosacea may be manifested by mild conjunctival irritation or inflammation of the meibomian (oil) glands on the eyelid margin. Chronic eyelid irritation can result in loss of eyelashes. No visual impairment accompanies the eyelid irritation.

Rosacea, in mild form, brings about a slight flushing of the nose and cheeks and, in some cases, the forehead and chin. However, in a severe form, lesions appear which are deep or purplish red and which include a chronic dilation of the superficial capillaries, i.e. telangiectasia. Also, in severe form, inflammatory acneiform pustules are present. Chronic involvement of the nose with rosacea in men can cause a bulbous enlargement known as rhinophyma. However, women are twice as likely as men to have rosacea. In women, this rhinophyma often takes the form of pimples and redness of or near the nose. Similarly, women are three times more likely than men to exhibit symptoms of perioral dermatitis, where redness and a rash appear above the upper lip attaching into the nose.

Another acute form of rosacea is known as granulomatous rosacea and, as such, is considered to be a distinctive form of the papular aspect of the disease. Therein, discreet pustules appear as yellowish brown nodules and as epithelioid cell granulomatous.

Rosacea may be diagnosed based on the presence of one or more of its manifestations. Patients with rosacea may have different triggering factors for the manifestations. These triggering factors may include, for example, any of genetic disposition, gastrointestinal disturbances (including dyspepsia with gastric hypochlorhydia and infestation with microaerophilic gram-negative bacteria *Helicobacter pylori*), hypertension, *Demodex folliculorum* mites, psychogenic factors, spicy foods, blushing, flushing, ultraviolet radiation, wind exposure, and stress. Often patients with rosacea are particularly susceptible to blushing and flushing, and signs of this may be an indicator of the probability of rosacea suffering later in life.

There are typically four stages of rosacea, as well as a predisposition to the condition. The stages can be defined as follows:

Pre-rosacea: skin flushes easily and redness lasts longer than normal and there is a family history of the condition.

Stage I: Frequent flushing, some persistent erythema.

Stage II: Persistent erythema and telangiectasias.

Stage III: Papules and pustules (plus Stage II).

Stage IV: Rhinophyma (bumpy, bulbous nose).

While certain lesions of rosacea may mimic lesions of acne vulgaris, the processes are separate and distinct. The principal differences between the two skin conditions are the presence of comedones (whiteheads and blackheads) in acne vulgaris only and not in rosacea, the characteristic mid-facial localization and flushing of rosacea not seen in acne, and the potential for eyelid involvement in rosacea which never occurs in acne. In fact, the clinical observation has been made that people who have classic acne vulgaris as teenagers rarely, if ever, develop full-blown rosacea as adults.

In the classic situation, rosacea is most common in adults between the ages of 20 and 84. For example, 63% of those people suffering from rosacea are between the ages of 20 and 59, while 27% of those people suffering from rosacea are between the ages of 60 and 84.

A further age breakdown shows that 19.1% of people suffering from rosacea are between the ages of 20 and 39; 47.4% are between the ages of 40 and 59; and 27.4% are between the ages of 60 and 84. Accordingly, the majority of rosacea sufferers have an age of at least 40 years.

The underlying cause of rosacea is unknown and has been a frequently discussed medical topic, with little consensus having ever been reached. Dietary influence, gastrointestinal disturbances, psychologic or hormonal imbalance, sebaceous gland abnormalities, and infection have all been considered but not validated as causes for rosacea. Other theories range from solar-induced dermal connective tissue damage, with resultant vascular distension, to humorally mediated active vasodilatory changes. A causative role has also been suggested for the hair follicle mite, *Demodex*, C. E. Bonnard, et al., *The Demodex Mite Population*, J. Amer. Acad. Dermatology, Vol. 28, No. 3, pp. 443-447, March 1993. After much discussion, at least four factors or co-factors have been suggested as the most likely causes of rosacea.

The first of these factors is endocrine related, as rosacea tends to occur most frequently in women. As such, one definite type of rosacea is believed to have a hormonal basis.

A second suggested factor is vasomotor lability, believed to have some connection with menopause, which brings about an impairment of normal or consistent flow of blood to the face and its capillaries. Excessive flow of blood to the face, i.e., the well-known "hot flashes" of menopause, is believed to constitute a factor in the disease and its pathogenesis. More particularly, it has been proven that increased skin temperature, as occurs in facial flushing, increases susceptibility to the condition.

The prominent presence of erythema (redness) and flushing of the face of affected persons with aggravation from heat, sunshine (particularly due to UV light), cold, chemical irritation, emotions, spices, coffee, tea, and alcohol, particularly in persons with a fair complexion, has focused attention on this vasomotor aspect of the disease. However, treatment with medications to block such vasomotor flushing has often had no effect on other aspects of the disease, such as papules and pustules. Further, rosacea-afflicted skin is abnormally sensitive to chemical and physical insults, while the frequent flushing and blushing in rosacea eventually leads to permanent skin redness.

As a third suggested factor, rosacea has been observed as a side effect or immune response to the use of certain cortisone products or standard acne medications, which can bring about a severe form of the condition. When topically applied to rosacea-affected skin, these medications generally irritate the skin and induce rosacea flare-ups. Similarly, agents that dilate blood vessels when ingested, for instance, ethanol and certain medications for high blood pressure, can bring on a rosacea blush when ingested by a person affected with rosacea. However, if untreated, rosacea can result in swollen veins, scattered lumps, and clusters of pustules on the face.

Finally, pathology analysis of the expressed contents of inflamed pustule follicles of the nose in acute rosacea has demonstrated the existence of demodices, which is a signature of the ectoparasite *Demodex folliculorum*. Accordingly, in such cases, a specific external pathogenic factor is evident. This factor is not present in acne.

Many skin disorders are treated with a single course of therapy on the premise that the etiology and presented symptoms are the result of a single cause. Unfortunately, many diseases, especially skin diseases, are complicated in that the symptoms may be the result of changes in internal, external, or a combination of both environments. Acne and rosacea have previously been identified as resulting from at least two of these conditions. As a result, conventional single agent therapies have been shown not to yield the desired clinical results in treating these diseases, such as, for example, cosmetic improvement (appearance), elimination of pathogenic organisms, reduction of swelling, etc.

Dietary avoidance of spicy foods and alcohol which cause flushing have in the past provided at most temporary symptomatic relief from rosacea. Jansen and Plewig, "Rosacea", *Clinical Dermatology* (Philadelphia: Lippincott-Raven Publishers, 1997; chapter 10-7) provide an excellent review of various treatments for rosacea in this regard.

Several potential treatments for rosacea have been disclosed in the art. However, none of these treatments have proven to be particularly effective. For example, U.S. Pat. No. 5,654,013 discloses a method of reducing inflammation in rosacea involving lightly rubbing a block of crystalline sodium chloride over moistened skin in affected areas. No claim was made for any antibiotic effect on bacteria or ectoparasites in the skin.

U.S. Pat. No. 3,867,522 similarly discloses the abrasive use of sodium chloride crystals rubbed over affected skin in acne and related disorders, again with no intended antibiotic effect and with the goal of treatment being the lessening of the severity of the disease and not a permanent or even a temporary cure.

Rosacea has also previously been treated with oral and/or topical antibacterial agents. The oral antibiotics used include tetracycline, erythromycin, and minocycline. This antibiotic treatment has been shown to effectively block progression of rosacea through a poorly-understood anti-inflammatory mechanism, but studies have shown that these medications do not act by killing either bacteria or *Demodex folliculorum* organisms in affected skin.

One particular antibiotic disclosed in U.S. Pat. No. 5,952,372 as effective for the oral treatment of rosacea is ivermectin (22,23-dihydroavermectin B1). However, it is uncertain whether ivermectin is orally effective in killing *Demodex folliculorum*, as the patent alleges.

Azoles, e.g. metronidazole and imidazoles, have also been previously used as treatments for rosacea, particularly for moderate to severe rosacea.

However, some patients suffering from rosacea have experienced adverse reactions to, or gain limited relief from, metronidazole containing compositions. Accordingly, compositions demonstrated to have a greater efficacy in treating rosacea than the currently available metronidazole compositions are still needed to provide greater, longer lasting, or more rapid relief to those suffering from this rosacea. However, such alternative compositions have not yet been recognized as more effective in treating rosacea than metronidazole containing compositions to date.

Sodium sulfacetamide with and without sulfur has been utilized for many years to treat acne. A nominal treatment concentration for sodium sulfacetamide is 10% and for sulfur is 5%. SULFACET R® (Dermik Laboratories, Inc. of Fort Washington, Pa.) is a marketed example of such products. However, such treatments have previously not been recognized as effective as compositions containing metronidazole for the treatment of rosacea.

Sulfur alone has been used to treat skin diseases, such as acne, for over 100 years. Sulfur products have been used at levels up to 10% to treat acne. Sulfur has also been combined with resorcinol to improve its performance. Again, however, sulfur alone has not previously been recognized as effective for treating rosacea.

In addition to such pharmaceutical treatments, limiting sun exposure has been suggested as an alternative, or combined, means for managing certain dermatological conditions. For example, A. P. Kelly (Principles and Practice of Dermatology, Sams and Lynch editors, 1990, p. 789) indicates that avoidance of sun exposure is a mechanism to be explored in the management of the skin flushing often seen with rosacea. Similarly, J. K. Wilkins stated (Id., p. 495) that "the degree to which reddening occurs results not only from the intensity of the flushing reaction, but also from the pigmentation of the subject and the visibility of the vessels, which may be enhanced in a sun-damaged dystrophic dermis." Accordingly, treatment regimens that in some way limit the exposure of skin to sunlight represent other possible alternatives for treating rosacea.

Sunscreens, for example, are designed to protect against sunburn caused by UVB rays, but generally provide little protection against UVA rays. UVA rays are linked to aging and generally have a depressing effect on the immune system and therefore may lead to other dermatological problems such as rosacea. In addition to preventing damage from exposure to UV radiation, the use of such UV absorbers to counteract the sensitizing effects of some dermatological therapeutics has been described in the art. For example, the use of UV absorbers in combination with erythromycin for the treatment of acne is described in U.S. Pat. No. 5,017,366.

There has been great difficulty in the art in preparing antibacterial compositions that can effectively be administered for treating skin diseases. For example, many of the presently known antibacterial compositions for dermatological treatment must remain stable for long periods of time (useful shelf life), not lose their potency (a known characteristic of antibiotics under certain conditions), not form insoluble substances or complexes because of the combining sulfacetamide and other active ingredients, and must minimize irritation to the skin. There is a lack of such antibacterial compositions in the art.

Accordingly, there remains a need in the art for stable topical compositions having a greater effectiveness in treating rosacea than the presently known compositions, such as the metronidazole containing compositions. The present subject matter addresses this need.

SUMMARY OF THE INVENTION

In one embodiment, the present subject matter is directed towards a topical composition for the treatment of mammalian skin dermatoses comprising a sulfacetamide or a derivative thereof and at least one sunscreen. This subject matter is also directed toward a method of treating mammalian dermatoses by administering a topical composition comprising a sulfacetamide or a derivative thereof and at least one sunscreen. This subject matter is also directed towards a topical composition for the treatment of mammalian skin dermatoses comprising sulfacetamide and at least one sunscreen, wherein the composition is chemically stable for more than 180 days at 25° C. This subject matter is also directed towards a topical composition for the treatment of mammalian skin dermatoses comprising sulfacetamide and at least one sunscreen, wherein the composition exhibits less than 10% decomposition of sulfacetamide or sunscreen after storage at 25° C. for 180 days.

In a preferred embodiment, the present subject matter relates to a method for treating rosacea in a patient comprising administering to a patient suffering from rosacea a first topical composition comprising at least one sulfacetamide or a derivative thereof and at least one sunscreen, wherein the administration of said first composition provides a more effective treatment of said rosacea in comparison to treatment of rosacea achieved by administration of a second topical composition comprising metronidazole.

In a further preferred embodiment, the present subject matter is directed to a method for treating inflammatory lesions in a patient comprising administering to a patient suffering from inflammatory lesions a first topical composition comprising at least one sulfacetamide or a derivative thereof and at least one sunscreen, wherein the administration of said first composition results in a higher decrease of inflammatory lesions in said patient in comparison to that achieved by administration of a second topical composition comprising metronidazole.

In yet another preferred embodiment, the present subject matter relates to a method for treating erythema in a patient comprising administering to a patient suffering from erythema a first topical composition comprising at least one sulfacetamide or a derivative thereof and at least one sunscreen, wherein the administration of said first composition results in a higher decrease of erythema in said patient in comparison to that achieved by administration of a second topical composition comprising metronidazole.

DETAILED DESCRIPTION OF THE INVENTION

In certain embodiments, the present subject matter relates to a composition comprising a sulfacetamide and a sunscreen in combination for the treatment of rosacea. This combination product is specifically directed to the multifaceted etiology of rosacea. The novel combination of sodium sulfacetamide and a sunscreen described herein offers the clinician a regimen which would be an effective treatment of this often unsightly skin condition, and in fact offers a more effective treatment than compositions presently known, such as MetroCream®.

The topical drug delivery system used herein may be aqueous, hydro-alcoholic, or non-aqueous in composition and may include polymers, liposomes, surfactants, thickeners, or other pharmaceutically acceptable ingredients which would enhance the product's acceptance. Such formulations are generally known in the art.

A preferred topical delivery system herein is an emulsion based delivery system. However, other topical pharmaceutical dosage forms, such as suspensions, should also be operative. The active ingredients may be dissolved, dispersed, suspended, solubilized, coated, entrapped, or encapsulated within the formulation matrix by a variety of techniques known in the art.

Acceptable levels of sodium sulfacetamide used in the present compositions are from 1 to 20%, more preferably 5 to 15%. Acceptable levels of sulfur used in the present compositions are from 1 to 20%, more preferably from 2.5 to 10%. While the preferred sulfacetamide is sodium sulfacetamide, other salts and derivatives which function in the treatment of mammalian skin dermatoses would also be suitable.

A variety of UV absorbers, sometimes referred to as "sunscreens", are known in the art and have varying effectiveness at absorbing different parts of the UV spectrum. In a preferred embodiment, the present compositions comprise a UV absorber component that has activity in both the UVA and UVB ranges. This may be accomplished either through the use of a UV absorber that is effective in both the UVA and the UVB ranges or through the use of two or more UV absorbers having combined activity across the UVA and UVB spectra.

UV absorbers encompassed herein include, but are not limited to, one or more of the following: benzophenone derivatives (such as benzophenone-1, benzophenone-2, or benzophenone-3 [also known as oxybenzone], benzophenone-4, benzophenone-6, benzophenone-8, benzophenone-12), alkyl and aryl cinnamate derivatives (such as DEA methoxycinnamate, octyl methoxycinnamate), aminobenzoate derivatives (such as p-aminobenzoic acid, ethyl dihydroxypropyl p-amino benzoic acid glyceryl p-aminobenzoic acid, octyl dimethyl p-aminobenzoic acid), homosalate, anthranilate derivatives (such as menthyl anthranilate), aryl acrylate derivatives (such as etocrylene, octocrylene), salicylate derivatives (such as octyl salicylate, trolamine salicylate), benzimidazole derivatives (such as 2-phenylbenzimidazole-5 sulphonic acid), benzilidene derivatives (such as 3-(4-methylbenzylidene)-camphor), benzoyl methane derivatives (such as 4-isopropyl dibenzoyl methane, butyl methoxy dibenzoyl methane [also known as avobenzone]) and oxides (such as titanium dioxide and zinc oxide).

The amount of UV absorber employed will depend on its effectiveness, alone or in combination with other UV absorbers, but in any event will be sufficient to block a measurable quantity of UV radiation, preferably that UV radiation generated naturally, such as by the sun, or generated by man-made UV radiation generating sources, such as electric lamps and beams. In a particularly preferred embodiment, one or more sunscreens are present and provide a sunscreen protection factor (SPF) of at least about 2. The most preferred UV absorbers and their concentration by weight is set forth in Table 1:

TABLE 1

UV Absorbers & Concentration

| UV Absorbers | % W/W |
|---|---|
| avobenzone | 0.1 to 5% |
| octocrylene | 0.1 to 15% |
| octyl methoxycinnamate | 0.1 to 10% |
| oxybenzone | 0.1 to 10% |

Compositions embodying the present subject matter are described in detail in the examples that follow. Examples 1 and 2 are most preferred.

EXAMPLE 1

Ingredients

The ingredients of Example 1 are set forth in Table 2.

TABLE 2

Example One Ingredients (% W/W)

| | % W/W |
|---|---|
| Phase A Ingredients | |
| Purified Water | 49.29 |
| Edetate Disodium | 0.500 |
| Sodium Phosphate Monobasic (Dihydrate) | 0.0100 |
| Phase B Ingredients | |
| Cetostearyl Alcohol | 1.50 |
| Steareth-2 | 2.25 |
| Steareth-21 | 2.75 |
| Emulsifying Wax, NF | 4.00 |
| Octyl Methoxycinnamate | 7.50 |
| $C_{12-15}$ Alkyl Benzoate | 5.00 |
| Propylene Glycol | 5.50 |
| Avobenzone | 3.00 |
| Dimethicone | 0.500 |
| Sodium Sulfacetamide | 10.7 |
| Precipitated Sulfur | 5.00 |
| Phase C Ingredients | |
| Purified Water | 1.00 |
| Benzyl Alcohol | 1.00 |
| Sodium Thiosulfate | 0.500 |
| To Make Total | 100.0 |

Directions for Preparation

Create Phase "A" by combining purified water, edetate disodium and sodium phosphate monobasic (dihydrate) in a suitable vessel. While mixing, heat Phase "A" to about 70° C. In a separate suitable container create Phase "B" by combining cetostearyl alcohol, steareth-2, steareth-21, emulsifying wax (NF), octyl methoxycinnamate, $C_{12-15}$ alkyl benzoate, propylene glycol, avobenzone and dimethicone. Heat Phase "B" to about 70° C. while mixing to make Phase "B" uniform. To Phase "B" add and disperse the sulfur and sodium sulfacetamide. Then add Phase "B" to Phase "A" while mixing and continue to mix for about 30 minutes. Cool the resulting mixture (Phase "AB") to about 40° C. while continuously mixing. Then add the benzyl alcohol to Phase "AB" and continue cooling and mixing. Add to Phase "AB" the sodium thiosulfate pre-dissolved in the purified water. Mix Phase "AB" until uniform.

Stability Testing

The composition of Example 1 was placed on stability at FT (Freeze-Thaw; a stability test where the composition is subject to alternating periods of freezing and warm environments), 6° C., 25° C., 30° C., and 40° C. All samples placed on stability were maintained at the constant temperature indicated.

The freeze thaw (FT) samples were subjected to alternate periods of freezing (−10 to −20° C.) and warmer environments, such as room temperature (15-30° C.). This test is used to accelerate emulsion and solution instability in hopes of finding problems early in development.

Each sample was observed weekly for the first four weeks and once a month for months two through six. Chemical analyses were completed on samples taken after storage at the designated temperatures for the stated number of days over a six month test period. The results of the chemical analyses are set forth in Table 3 below and the physical observations are set forth in Table 4 below.

TABLE 3

Example One Chemical Analysis

| Ingredient | # Days | Specification (% W/W) | FT | 6° C. | 25° C. | 30° C. | 40° C. |
|---|---|---|---|---|---|---|---|
| Sodium Sulfacetamide | 7 | 9-11 | | | 10.84 | | |
| Sodium Sulfacetamide | 96 | 9-11 | 10.68 | 10.87 | 10.54 | 10.40 | 10.36 |
| Sodium Sulfacetamide | 186 | 9-11 | | 10.94 | 10.70 | 10.61 | 10.06 |
| Sulfur | 7 | 4.5-5.0 | | | 4.75 | | |
| Sulfur | 96 | 4.5-5.0 | 4.88 | 4.79 | 5.10 | 4.91 | 5.04 |
| Sulfur | 186 | 4.5-5.0 | | 4.63 | 4.65 | 4.85 | 5.04 |
| Avobenzone | 7 | 2.7-3.30 | | | 3.00 | | |
| Avobenzone | 96 | 2.7-3.30 | 2.98 | 2.97 | 2.95 | 2.93 | 2.93 |
| Avobenzone | 186 | 2.7-3.30 | | 2.92 | 2.92 | 2.93 | 2.88 |
| Octyl Methoxycinnamate | 7 | 6.75-8.25 | | | 6.89 | | |
| Octyl Methoxycinnamate | 96 | 6.75-8.25 | 7.48 | 7.42 | 7.29 | 7.39 | 7.56 |
| Octyl Methoxycinnamate | 186 | 6.75-8.25 | | 7.48 | 7.44 | 7.44 | 7.50 |
| Benzyl Alcohol | 96 | 0.90-1.10 | 1.12 | 0.99 | 1.01 | 1.01 | 0.97 |
| Benzyl Alcohol | 186 | 0.90-1.10 | | 0.99 | 1.00 | 1.01 | 0.98 |

TABLE 3-continued

Example One Chemical Analysis

| Ingredient | # Days | Specification (% W/W) | FT | 6° C. | 25° C. | 30° C. | 40° C. |
|---|---|---|---|---|---|---|---|
| pH | 96 | NA | 7.42 | 7.39 | 7.39 | 7.43 | 7.42 |
| pH | 186 | NA |  | NA | 7.22 | NA | 7.25 |

TABLE 4

Example One Physical Appearance

| Day | Temperature | Appearance |
|---|---|---|
| 0 | 25° | A pale yellow smooth homogenous cream |
| 7 | All | Same as initial |
| 14 | All | Same as initial |
| 21 | All | Same as initial |
| 28 | All | Same as initial |
| 53 | 40° | Same as initial with slight aeration |
| 53 | All others | Same as initial |
| 95 | FT, 6°, 25° | Same as initial. |
| 95 | 30° | Same as initial with slight aeration |
| 95 | 40° | Product has darkened and become aerated. |
| 186 | All | Same as day 95 |

EXAMPLE 2

Ingredients

The ingredients of Example 2 are set forth in Table 5.

TABLE 5

Example Two Ingredients (% W/W)

|  | % W/W |
|---|---|
| Phase A Ingredients |  |
| Purified Water | 43.79 |
| Edetate Disodium | 0.500 |
| Sodium Phosphate Monobasic (Dihydrate) | 0.0100 |
| Phase B Ingredients |  |
| Cetostearyl Alcohol | 1.50 |
| Steareth-2 | 2.25 |
| Steareth-21 | 2.75 |
| Emulsifying Wax, NF | 4.00 |
| Oxybenzone | 6.00 |
| $C_{12-15}$ Alkyl Benzoate | 5.00 |
| Propylene Glycol | 5.50 |
| Octocrylene | 10.0 |
| Dimethicone | 0.500 |
| Sodium Sulfacetamide | 10.7 |
| Precipitated Sulfur | 5.00 |
| Phase C Ingredients |  |
| Purified Water | 1.00 |
| Benzyl Alcohol | 1.00 |
| Sodium Thiosulfate | 0.500 |
| To Make Total | 100.0 |

Directions for Preparation

Create Phase "A" by combining purified water, edetate disodium and sodium phosphate monobasic (dihydrate) in a suitable vessel. While mixing, heat Phase "A" to about 70° C. In a separate suitable container create Phase "B" by combining cetostearyl alcohol, steareth-2, steareth-21, emulsifying wax (NF), oxybenone, $C_{12-15}$ alkyl benzoate, propylene glycol, octocrylene and dimethicone. Heat Phase "B" to about 70° C. while mixing to make Phase "B" uniform. To Phase "B" add and disperse the sulfur and sodium sulfacetamide. Then add Phase "B" to Phase "A" while mixing and continue to mix for about 30 minutes. Cool the resulting mixture (Phase "AB") to about 40° C. while continuously mixing Phase "AB". Then add the benzyl alcohol to Phase "AB" and continue cooling and mixing. Add to Phase "AB" the sodium thiosulfate pre-dissolved in the purified water. Mix phase "AB" until uniform.

The formulation of Example Two was stored in clear vials capped with black polyseal lined screw caps and tested for stability at 40° C., 30° C., 25° C., 6° C. and FT. The samples were observed and assayed at 7 days and 3 months.

Stability Testing

The composition of Example 2 was placed on stability at FT, 6° C., 25°, 20° C., 30° C., and 40° C. Each sample was observed weekly for the first four weeks and once a month for months two through six. Chemical analyses were completed on samples taken after storage at the designated temperatures for the stated number of days over a six month test period. The results of the chemical analyses are set forth in Table 6 below and the physical observations are set forth in Table 7 below.

TABLE 6

Example Two Chemical Analysis

| Ingredient | # Days | Specification (% W/W) | FT | 6° C. | 25° C. | 30° C. | 40° C. |
|---|---|---|---|---|---|---|---|
| Sodium Sulfacetamide | 7 | 9-11 | | | 10.60 | | |
| Sodium Sulfacetamide | 96 | 9-11 | 10.67 | 10.61 | 10.68 | 10.34 | 10.19 |
| Sulfur | 7 | 4.5-5.0 | | | 4.63 | | |
| Sulfur | 96 | 4.5-5.0 | 4.97 | 4.92 | 5.12 | 5.45 | 5.36 |
| Octocrylene | 7 | 9.00-11.00 | | | 9.54 | | |
| Octocrylene | 96 | 9.00-11.00 | 9.60 | 9.61 | 9.64 | 8.89 | 9.37 |
| Oxybenzone | 7 | 5.4-6.6 | | | 5.86 | | |
| Oxybenzone | 96 | 5.4-6.6 | 5.99 | 5.97 | 5.99 | 5.51 | 5.84 |
| Benzyl Alcohol | 96 | 0.9-1.10 | .90 | .92 | .90 | .90 | .88 |
| PH | 96 | NA | 7.35 | 7.43 | 7.46 | 7.53 | 7.55 |

TABLE 7

Example Two Physical Appearance

| Day | Temperature | Appearance |
|---|---|---|
| 0 | 25° | A pale yellow smooth homogenous cream |
| 7 | 40° | Slight darkening of product, but otherwise as initial |
| 7 | All others | Same as initial |
| 14 | All | Same as day 7 |
| 21 | 30° | Slightly darker than day 7 |
| 21 | 40° | Same as day 7 |
| 21 | All others | Same as initial |
| 28 | All | Same as day 21 |
| 53 | 40° | Same as day 21 with slight aeration |
| 53 | All others | Same as day 28 |
| 95 | FT, 6°, 25° | As initial with very slight aeration |
| 95 | 30° | Product has darkened and become aerated |
| 95 | 40° | Product has become aerated. A brown layer has formed on the bottom ⅓ of the vial with the remaining product being slightly green in color |
| 186 | 25° | Aeration more pronounced than at 95 days |
| 186 | All others | Same as day 95 |

EXAMPLE 3

Ingredients

The ingredients of Example 3 are set forth in Table 8.

TABLE 8

Example Three Ingredients (% W/W)

| | % W/W |
|---|---|
| Phase A Ingredients | |
| Purified Water | 46.29 |
| Edetate Disodium | 0.500 |
| Sodium Phosphate Monobasic (Dihydrate) | 0.0100 |
| Phase B Ingredients | |
| Cetostearyl Alcohol | 2.00 |
| Steareth-2 | 2.00 |
| Steareth-21 | 3.00 |
| Emulsifying Wax, NF | 5.00 |
| Avobenzone | 1.00 |
| C$_{12-15}$ Alkyl Benzoate | 5.00 |
| Propylene Glycol | 4.00 |
| Octyl Methoxycinnamate | 5.00 |
| Dimethicone | 0.500 |
| Zinc Oxide Dispersion | 3.50 |
| Titanium Dioxide Dispersion | 4.00 |
| Sodium Sulfacetamide | 10.7 |
| Precipitated Sulfur | 5.00 |
| Phase C Ingredients | |
| Purified Water | 1.00 |
| Benzyl Alcohol | 1.00 |
| Sodium Thiosulfate | 0.500 |
| To Make Total | 100.0 |

Directions for Preparation

Create Phase "A" by combining the purified water, edetate disodium, and sodium phosphate monobasic (dihydrate) in a suitable vessel. While mixing, heat Phase "A" to about 70° C. In a separate suitable container create Phase "B" by combining cetostearyl alcohol, steareth-2, steareth-21, emulsifying wax (NF), C$_{12-15}$ alkyl benzoate, propylene glycol, and dimethicone. Heat Phase "B" to about 70° C. while mixing to make Phase "B" uniform. To Phase "B" add and disperse the sulfur, sodium sulfacetamide, zinc oxide and titanium dioxide. Then add Phase "B" to Phase "A" while mixing and continue to mix for about 30 minutes. Cool the resulting mixture (Phase "AB") to about 40° C. while continuously mixing Phase "AB". Then add the benzyl alcohol to Phase "AB" and continue cooling and mixing. Add to Phase "AB" the sodium thiosulfate pre-dissolved in the purified water. Mix Phase "AB" until it is uniform.

Compositions as disclosed herein may be administered to a patient suffering from rosacea by thinly applying the composition topically to affected areas of the face 1-3 times per day.

SPF Testing (In Vitro)

Ten (10) compositions with varying sunscreen components were tested to determine their relative sunscreen protection factor using an in vitro procedure employing the Optometrics SPF290 instrument (available from Optometrics LLC of Ayer, Mass.). The ten formulations were made according to the procedures set out in Examples 1, 2 and 3 with the only variable being the sunscreen components. Data were generated using as a substrate Transpore® surgical tape, available from 3M Corp. of St. Paul, Minn. Test materials are applied to the tape and the UV light absorbance measured. Results generated are reported in Table 9. These measurements provide an assessment of potential product SPF, the true value of which may only be established in a human clinical evaluation.

TABLE 9

SPF (In Vitro) Testing Results

| Formulation Components | SPF Value | +/− SD |
|---|---|---|
| Sodium Sulfacetamide 10% | 14.9 | 3.0 |
| Sulfur 5% | | |
| Avobenzone 3% | | |
| Octyl Methoxycinnamate 7.5% | | |
| Oxybenzone 6% | | |
| Sodium Sulfacetamide 10% | 12.1 | 2.6 |
| Sulfur 5% | | |
| Avobenzone 3% | | |
| Octocrylene 10% | | |
| Octyl Methoxycinnamate 7.5% | | |
| Sulfacetamide Sodium 10% | 11.9 | 2.0 |
| Sulfur 5% | | |
| Octocrylene 10% | | |
| Octyl Methoxycinnamate 7.5% | | |
| Oxybenzone 6% | | |
| Sodium Sulfacetamide 10% | 8.3 | 1.2 |
| Sulfur 5% | | |
| Octyl Methoxycinnamate 7.5% | | |
| Octocrylene 10% | | |
| Octyl Salicylate 5.0% | | |
| Sodium Sulfacetamide 10% | 10.4 | 2.3 |
| Sulfur 5% | | |
| Octyl Methoxycinnamate 7.5% | | |
| Sulisobenzone 10% | | |
| Sodium Sulfacetamide 10% | 8.3 | 0.7 |
| Sulfur 5% | | |
| Octocrylene 10% | | |
| Octyl Methoxycinnamate 7.5% | | |
| Sodium Sulfacetamide 10% | 11.4 | 3.7 |
| Sulfur 5% | | |
| Avobenzone 3% | | |
| Octyl Methoxycinnamate 7.5% | | |
| Sodium Sulfacetamide 10% | 1.6 | 0.1 |
| Sulfur 5% | | |
| Sodium Sulfacetamide 10% | 12.2 | 2.9 |
| Sulfur 5% | | |
| Octocrylene 10% | | |
| Oxybenzone 6% | | |
| Sodium Sulfacetamide 10% | 11.6 | 2.2 |
| Sulfur 5% | | |
| Avobenzone 3% | | |
| Octyl Methoxycinnamate 7.5% | | |

Data generated show that the addition of sunscreen agents increases the relative SPF values found when compared to the product without added sunscreens.

SPF Testing (In Vivo)

Five of the above compositions were tested with a homosalate control to determine their relative sunscreen protection factor. The tests were conducted by following an FDA approved human clinical study design. Forty-six subjects (43 female, 3 male) were enrolled in the study, each subject having one of the following skin types and sunburn and tanning histories: I) always burns easily; never tans (sensitive), II) always burns easily; tans minimally (sensitive), III) burns moderately; tans gradually (normal). Each subject's inherent MED (minimal erythema dose) was determined by exposing the unprotected skin on their backs to ultraviolet radiation in a series of doses or timed intervals. Twenty-two to twenty-four hours post exposure the series of doses were evaluated to determine the smallest dose of energy that produced redness reaching the borders of the exposure site (MED). This procedure was repeated concurrently with the test products for confirmation (MED Unprotected Control Site).

The subjects were sequentially placed into two groups. Group 1 tested the first two test articles (as listed in Table 10) and the 8% homosalate control and Group 2 tested the second three test articles (as listed in Table 10) and the 8% homosalate control (applied to their backs) with the sequence of test articles predetermined by randomization. A series of seven ultraviolet radiation exposures were administered within each treatment area as outlined in the FDA Final Monograph.

Following exposure of the sub sites to ultraviolet radiation, a visual evaluation was conducted for the presence or absence of an immediate response (darkening, reddening, or heat response) and noted. The sub sites were covered and evaluated 22-24 hours after exposure, in a blinded manner, to determine the MED. Reactions to the ultraviolet exposures were graded using a scale of 0-3+ where 0=no reaction, ±=minimal erythema, the first perceptible, redness reaction with clearly defined borders, 1+=defined erythema, 2+=moderate erythema, and 3+=severe erythema. Results generated are reported in Table 10.

For each subject, the SPF value for each test article sunscreen was calculated by dividing the dose of ultraviolet radiation (joules/cm$^2$ required to produce the MED of the protected skin (MED Protected Skin) by the dose of ultraviolet radiation (joules/cm$^2$ required to produce the MED of the unprotected skin (MED Unprotected Control Site).

The label SPF value for each test article formulation was determined as follows. First, the mean SPF value (x) was calculated. The standard deviation (s) was determined. The upper 5% point was obtained from the t distribution table with n−1 degrees of freedom (t). Next $ts/\sqrt{n}$ was computed and denoted by (A). The label SPF was determined to be the largest whole number less than x−A. (See the FDA Final Monograph: FR May 21, 1999, Vol. 64, No. 98). It is recommended that the standard error be determined and not exceed five percent of the mean.

TABLE 10

SPF (In Vivo) Testing Results

| Formulation Description | SPF Value | ± SD | Label SPF |
|---|---|---|---|
| Sodium Sulfacetamide 10% | 20.6 | 2.6 | 19 |
| Sulfur 5% | | | |
| Avobenzone 3% | | | |
| Oxybenzone 6% | | | |
| Octyl Methoxycinnamate 7.5% | | | |
| Sodium Sulfacetamide 10% | 19.9 | 1.8 | 19 |
| Sulfur 5% | | | |
| Avobenzone 3% | | | |
| Octocrylene 10% | | | |
| Octyl Methoxycinnamate 7.5% | | | |
| Sodium Sulfacetamide 10% | 20.4 | 3.4 | 18 |
| Sulfur 5% | | | |
| Octocrylene 10% | | | |
| Octyl Methoxycinnamate 7.5% | | | |
| Oxybenzone 6% | | | |
| Sodium Sulfacetamide 10% | 20.1 | 3.2 | 18 |
| Sulfur 5% | | | |
| Octocrylene 10% | | | |
| Octyl Methoxycinnamate 7.5% | | | |
| Sodium Sulfacetamide 10% | 20.3 | 3.4 | 18 |
| Sulfur 5% | | | |
| Avobenzone 3% | | | |
| Octyl Methoxycinnamate 7.5% | | | |

Data generated show each of the compositions exhibit a sun protection factor.

Metronidazole Comparative Study (In Vivo)

A clinical study was carried out to compare the efficacy and safety of the present compositions to a currently marketed rosacea treatment having metronidazole as the active ingredient. The study was a double-blind, parallel group study in which approximately 140 subjects (20-32 subjects/site for six sites) with rosacea were randomly assigned to twice daily treatment with either of two compositions for twelve weeks. The first composition comprised the composition of Example 1 comprising a 10% sodium sulfacetamide and 5% sulfur cream with sunscreens. The second composition comprised the commercially available MetroCream® composition comprising 0.75% metronidazole, available from Galderma International of La Defense Cedex, France.

Study subjects were required to be at least 16 years of age and to have clinical evidence of rosacea with a minimum of 10 and a maximum of 39 inflammatory lesions (papules and pustules), at least moderate erythema, and at least an investigator global severity of moderate. Subjects were not allowed to use medicated cleansers containing benzoyl peroxide, sodium sulfacetamide, or salicylic acid, or rosacea or acne treatments of any type including miticides, pediculocides, and corticosteroids, for defined periods of time before study entry and throughout the study. Subjects were excluded from study entry if they used cimetidine, lithium, disulfiram, coumarin anticoagulants, niacin, frequently used vasodilators with known flushing activity, or any medication that would interfere with the study results. Subjects were to minimize the use of spicy foods, very hot foods and drinks, caffeinated and alcoholic beverages, and exposure to sunlight including sunlamps during the study.

Efficacy and safety were evaluated initially (week 0) and at all subsequent visits (weeks 3, 6, 9, and 12). Evaluation of efficacy was performed by counting total facial inflammatory lesions (papules and pustules) and grading facial erythema and global rosacea severity at all visits. Subject's assessment of global improvement relative to the subject's initial condition was also made at weeks 3, 6, 9, and 12.

Seventy-five subjects were entered to test the composition of Example 1, and 77 subjects were entered into the MetroCream® (group for a total of 152 subjects. One hundred and thirty-eight subjects completed the study with ten dropouts in the Example 1 group and four dropouts in the MetroCream® group. The demographic and baseline features of the subjects were similar for both groups. The demographic population consisted primarily of female Caucasian adults.

Data analyses for efficacy were performed on all subjects who had data after baseline regardless of whether the protocol was followed (intent to treat subjects) with imputations made by carrying forward the last available observation. Statistical methods included analyses of variance for lesion count data and the Cochran-Mantel-Haenszel procedure for categorical data. Effects considered were site and treatment.

The primary efficacy variable, symmetrized percent reduction from baseline of inflammatory lesion counts, was significantly greater for the composition of Example 1 than MetroCream® at week 12. The least square mean symmetrized percent reduction was back calculated to 80% reduction for the composition of Example 1 and 72% reduction for MetroCream®. There was no difference for the other primary efficacy variable, proportion of subjects with success for investigator global severity (reduction from baseline by at least 2 grades), at week 12 for the composition of Example 1 (78%) compared to the MetroCream® group (68%). For the secondary efficacy variables, the Example 1 group had a significantly greater proportion of subjects (69%) with improvement in erythema score (reduction by at least 1 grade) at week 12 than the MetroCream® group (45%), and success with subject global improvement (cleared, excellent or good) at week 12 was also significantly greater for the composition of Example 1 (79%) than for MetroCream® (59%).

TABLE 11

Comparison of Results at Week 12 for All Subjects

| Parameter | Example 1 | MetroCream |
|---|---|---|
| Number of subjects enrolled | 75 | 77 |
| Mean age in years | 48 | 46 |
| Percent male/female | 28/72 | 29/71 |
| Investigator Global Severity | | |
| % of subjects with success at week 12 | 78 | 68 |
| p-value: comparison to MetroCream | 0.1894 | NA |
| Inflammatory lesions | | |
| LS Mean[a] % reduction at week 12 | 80 | 72 |
| p-value: comparison to MetroCream using symmetrized % reduction | 0.0424 | NA |
| Erythema | | |
| % of subjects with improved erythema at week 12 | 69 | 45 |
| p-value: comparison to MetroCream | 0.0007 | NA |
| Subject Global Improvement | | |
| % of subjects with cleared, excellent, or good at week 12 | 79 | 59 |
| p-value: comparison to MetroCream | 0.0131 | NA |
| Overall Tolerance (all subjects) % of subjects with good or excellent | 88% | 100% |

[a]LS Mean = least square mean (from analysis of variance with effects for site and treatment)

Overall, this study suggests that twice daily use of the composition of Example 1 is an effective regimen for the treatment of rosacea and is more effective than metronidazole treatments. In particular, the present compositions appear to be significantly more effective than currently available treatments, notably those having metronidazole as the sole active ingredient. In particular, the present compositions appear to be more effective than MetroCream®, a specific metronidazole based treatment. Such metronidazole based treatments are presently considered by some to be the treatment of choice for rosacea. This result is unexpected given the previously studied treatments using sulfacetamide. The enhanced efficacy of the compositions as demonstrated herein is believed to result from the present unique combination of a sulfacetamide or a derivative thereof and a sunscreen.

Accordingly, it would further be expected that the use of the composition of Example 1 is more effective than topical metronidazole treatments comprising about 0.5% to about 1.5% metronidazole in the treatment of rosacea. In particular, it would be expected that the present compositions are more effective than topical metronidazole treatments comprising about 0.75% or about 1% metronidazole in the treatment of rosacea.

Additionally, it would be expected that the results herein described would be similarly observed for any period of treatment or treatment regimen useful in treating rosacea.

This includes daily administration of the compositions during the period of treatment, twice daily administration of the topical compositions, or intermittent administration of the topical compositions. Further, the period of treatment contemplated herein can be any sufficient period of time to observe a reduced incidence of said rosacea, for example from about 6 to about 12 weeks, but in most cases more than 3 weeks, minumum.

Intermittent administration contemplated herein includes administration conducted other than daily (i.e. twice weekly) administration. Such intermittent administration is typically conducted when a patient commences a new treatment, as a treatment is in its final stages (i.e. as the patient is weaned off of the treatment), or as part of a maintenance regimen. Typically, intermittent administration is conducted more than once per week but less than once per day. This intermittent treatment is especially useful when a patient starts a new treatment regimen to build their tolerance to the new medicine, and is typically followed by a more regular administration regimen.

Accordingly, further contemplated herein is the intermittent administration of the topical composition after said period of treatment has ended to maintain the reduced incidence of rosacea.

The present subject matter being thus described, it will be obvious that the same may be modified or varied in many ways. Such modifications and variations are not to be regarded as a departure from the spirit and scope of the present subject matter and all such modifications and variations are intended to be included within the scope of the following claims.

What is claimed is:

1. A method for treating rosacea in a patient comprising administering to a patient suffering from rosacea a first topical composition comprising at least one sulfacetamide or a derivative thereof and at least one sunscreen, wherein the administration of said first composition provides a more effective treatment of said rosacea in comparison to treatment of rosacea achieved by administration of a second topical composition comprising metronidazole.

2. The method of claim 1, wherein the second topical composition comprising metronidazole consists essentially of metronidazole.

3. The method of claim 1, wherein, in the second topical composition comprising metronidazole, metronidazole is the sole active ingredient.

4. The method of claim 1, wherein the second topical composition comprises about 0.75% metronidazole.

5. The method of claim 1, wherein said increased treatment of rosacea results in a higher decrease of inflammatory lesions in said patient in comparison to that achieved by said administration of said second topical composition comprising metronidazole.

6. The method of claim 5, wherein administration of said first topical composition provides at least an 8% higher decrease of inflammatory lesions in said patient in comparison to that achieved by said administration of said second topical composition.

7. The method of claim 1, wherein said increased treatment of rosacea results in a higher decrease of erythema in said patient in comparison to that achieved by said administration of said topical composition comprising metronidazole.

8. The method of claim 7, wherein administration of said first topical composition provides at least a 24% higher decrease of erythema in said patient in comparison to that achieved by said administration of said second topical composition.

9. The method of claim 1, wherein said increased treatment is measured after at least 12 weeks of treatment with said topical compositions.

10. The method of claim 1, wherein said administration comprises administering said topical compositions to said patient each day during a period of treatment.

11. The method of claim 1, wherein said administration comprises intermittent administration of said topical compositions.

12. The method of claim 1, wherein said sulfacetamide is sodium sulfacetamide.

13. The method of claim 1, wherein said first composition comprises about 5 to about 15% by weight of said at least one sulfacetamide or a derivative thereof.

14. The method of claim 1, wherein said first topical composition further comprises sulfur.

15. The method of claim 14, wherein said first topical composition comprises about 2.5 to about 10% by weight of said sulfur.

16. The method of claim 1, wherein said first composition comprises at least two different sunscreens.

17. The method of claim 1, wherein said sunscreen is selected from the group consisting of avobenzone, octocrylene, octyl methoxycinnamate, oxybenzone, titanium dioxide, zinc oxide, and mixtures thereof.

18. The method of claim 1, wherein said first composition comprises about 0.1 to about 10% by weight of said at least one sunscreen.

19. The method of claim 1, wherein said at least one sunscreen is present in an amount sufficient to produce a sun protection factor of at least 2.

20. A method for treating inflammatory lesions in a patient comprising administering to a patient suffering from inflammatory lesions a first topical composition comprising at least one sulfacetamide or a derivative thereof and at least one sunscreen, wherein the administration of said first composition results in a higher decrease of inflammatory lesions in said patient in comparison to that achieved by administration of a second topical composition comprising metronidazole.

21. The method of claim 20, wherein the second topical composition comprising metronidazole consists essentially of metronidazole.

22. The method of claim 20, wherein, in the second topical composition comprising metronidazole, metronidazole is the sole active ingredient.

23. The method of claim 20, wherein the second topical composition comprises about 0.5% to about 1.5% metronidazole.

24. The method of claim 20, wherein administration of said first topical composition provides at least an 8% higher decrease of inflammatory lesions in said patient in comparison to that achieved by said administration of said second topical composition.

25. The method of claim 20, wherein said decrease of inflammatory lesions is measured after at least 12 weeks of treatment with said topical compositions.

26. The method of claim 20, wherein said administration comprises twice daily administration of said topical composition to said patient.

27. A method for treating erythema in a patient comprising administering to a patient suffering from erythema a first topical composition comprising at least one sulfacetamide or a derivative thereof and at least one sunscreen, wherein the administration of said first composition results in a higher decrease of erythema in said patient in comparison to that achieved by administration of a second topical composition comprising metronidazole.

28. The method of claim 27, wherein the second topical composition comprising metronidazole consists essentially of metronidazole.

29. The method of claim 27, wherein, in the second topical composition comprising metronidazole, metronidazole is the sole active ingredient.

30. The method of claim 27, wherein the second topical composition comprises about 0.5% to about 1.5% metronidazole.

31. The method of claim 27, wherein administration of said first topical composition provides at least a 24% higher decrease of erythema in said patient in comparison to that achieved by said administration of said second topical composition.

32. The method of claim 27, wherein said decrease of erythema is measured after at least 12 weeks of treatment with said topical compositions.

33. The method of claim 27, wherein said administration comprises at least once a day administration of said topical composition to said patient during the treatment regimen.

34. The method of claim 1, wherein said administration comprises twice daily administration of said topical composition to said patient.

35. The method of claim 10, wherein said period of treatment comprises a sufficient period of time to observe a reduced incidence of said rosacea.

36. The method of claim 10, wherein said period of treatment is from about 6 to about 12 weeks.

37. The method of claim 10, wherein said patient is intermittently administered said topical composition after said period of treatment.

38. The method of claim 11, wherein said intermittent administration is conducted when said patient commences said treatment, as said treatment is in its final stages, or as part of a maintenance regimen.

39. The method of claim 11, wherein said intermittent administration comprises administration of said topical compositions to said patient more than once per week but less than once per day.

40. The method of claim 1, wherein said sunscreen blocks the absorption of UV radiation.

41. The method of claim 1, wherein said sunscreen absorbs UV A and UV B radiation.

42. The method of claim 1, wherein said sunscreen is an inorganic oxide.

43. The method of claim 1, wherein said first topical composition further comprises benzyl alcohol.

* * * * *